(12) United States Patent
Benedict et al.

(10) Patent No.: US 8,323,969 B2
(45) Date of Patent: Dec. 4, 2012

(54) PREPARATION OF REGULATORY T CELLS USING ICAM-1 CO-STIMULATION

(75) Inventors: Stephen H. Benedict, Lawrence, KS (US); Kelli M. Cool, Lawrence, KS (US); Abby L. Dotson, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 277 days.

(21) Appl. No.: 12/122,377

(22) Filed: May 16, 2008

(65) Prior Publication Data

US 2008/0286245 A1    Nov. 20, 2008

Related U.S. Application Data

(60) Provisional application No. 60/930,922, filed on May 18, 2007.

(51) Int. Cl.
*C12N 5/071* (2010.01)
*C12N 5/00* (2006.01)
*C12N 5/02* (2006.01)

(52) U.S. Cl. ..................... 435/372.3; 435/377

(58) Field of Classification Search .......... None
See application file for complete search history.

(56) References Cited

U.S. PATENT DOCUMENTS

| | | | |
|---|---|---|---|
| 2006/0051350 A1 | 3/2006 | Van Oosterhout et al. | |
| 2006/0067912 A1* | 3/2006 | Horwitz | 424/85.2 |
| 2006/0233751 A1 | 10/2006 | Bluestone et al. | |
| 2008/0131445 A1* | 6/2008 | Bluestone et al. | 424/184.1 |

OTHER PUBLICATIONS

Zheng et al., 2004, J. Immunol. vol. 172: 5213-5221.*
Gregori et al., 2003, J. Immunol. vol. 171: 4040-4047.*
Faustman et al., 2010. Nature Reviews. vol. 9: 482-493.*
Cool et al. Apr. 2007, J. Immunol. vol. 178: 88:32, pp. 1-2.*
Kohlmeier et al., *Costimulation of naive human CD4 T cells through intercellular adhesion molecule-1 promotes differentiation to a memory phenotype that is not strictly the result of multiple rounds of cell division*, Immunology, Aug.118(4) 549-558 (2006).
Kohlmeier et al., *The outcome of T-cell costimulation through intercellular adhesion molecule-1 differs from costimulation through leucocyte function-associated antigen-1*, Immunology, Feb. 108(2) 152-157 (2003).
Chirathaworn et al., *Stimulation through intercellular adhesion molecule-1 provides a second signal for T cell activation*, J. Immunol., Jun. 1 168(11) 5530-5537 (2002).
Vukmanovic-Stejic et al., *Human CD4+ CD25hi Foxp3+ regulatory T cells are derived by rapid turnover of memory populations in vivo*, Journal of Clinical Investigation, Sep. 1, 2006, vol. 116, No. 9, pp. 2423-2433 (p. 2423, abstract; p. 2429, col. 2, para 2).
Banham et al., *FOXP3+ regulatory T cells: Current controversies and future perspectives*, European Journal of Immunology, Nov. 2006, vol. 36, No. 11, pp. 2832-2836 (p. 2834, col. 1, para. 3).

* cited by examiner

*Primary Examiner* — Amy Juedes
(74) *Attorney, Agent, or Firm* — Stinson Morrison Hecker LLP

(57) ABSTRACT

A method for generating a purified regulatory T cell composition having a $CD4^+CD25^+Foxp3^-$ phenotype from naive T cells having $CD4^+CD45RA^+RO^-CD11a^{lo}\,CD27^+$ phenotype comprising the steps of stimulating a T cell receptor on the naive T cells and stimulating ICAM-1 on the naive T cells.

18 Claims, 12 Drawing Sheets

PREPARATION OF REGULATORY T CELLS USING ICAM-1 CO-STIMULATION

CROSS-REFERENCE TO RELATED APPLICATIONS

This application is based on and claims priority to U.S. Provisional Application Ser. No. 60/930,922 filed on May 18, 2007, which is hereby incorporated herein by reference.

STATEMENT REGARDING FEDERALLY SPONSORED RESEARCH OR DEVELOPMENT

The invention was made with Government support under Grant No. AG023946 awarded by NIH—National Institute of Aging and Grant No. DK073119 awarded by NIH—National Institute of Diabetes and Digestive and Kidney Disorders. The Government has certain rights in the invention.

FIELD OF THE INVENTION

The present invention relates generally to methods for stimulating and activating naive T cells, and more particularly, to methods to differentiate the naive T cells into regulatory T cells in very high numbers.

BACKGROUND OF THE INVENTION

Immune tolerance is central to the immune system's ability to differentiate between self and foreign proteins. Central tolerance is initially achieved during thymic selection by the deletion of self-reactive T cells. However, central tolerance is incomplete, and further immune regulation is required in the periphery. Peripheral mechanisms of T cell regulation include the induction of anergy, activation induced cell death, and regulatory T cells.

Within the $CD4^+$ T lymphocyte cell population, several categories of regulatory T cells have been described. In general, these subpopulations are classified according their site of development and/or the cytokines they produce. One subset of regulatory T cells develops in the thymus (natural regulatory T cells) while a different subset differentiates from $CD4^+CD25^-$ precursors after leaving the thymus and encountering specific antigen in the periphery (inducible regulatory T cells). Among inducible regulatory T cell subsets, Tr1 cells secrete IL-10, while Th3 cells secrete TGF-β, although both cell types have been shown to produce both IL-10 and TGF-β to some extent. More recently, investigators have shown that the expression of forkhead box protein P3 ("Foxp3") transcription factor is an important marker in the classification of regulatory T cells.

Given the important role $CD4^-CD25^+$ regulatory T cells play in immune tolerance, there is a need to develop methods for generating, selecting, and expanding human antigen-specific regulatory $CD4^+CD25^+$ T cells from the peripheral blood of a subject in need thereof for use in the treatment and/or prevention of autoimmune disorders, allergies, inflammatory conditions and for the prevention of graft rejection in a recipient following solid organ, tissue, bone marrow, or stem cell transplantation.

BRIEF SUMMARY OF THE INVENTION

The present invention is directed to a method of differentiating naive T cells into a regulatory T cell phenotype using TCR (CD3) stimulation along with Intercellular Adhesion Molecule-1 or ICAM-1 ("CD54") as a co-stimulatory signal. The regulatory T cells are substantially separated from other cells to create a purified regulatory T cell composition. The regulatory T cells have the potential to generate T cell compositions useful in the treatment of a wide variety of aberrant immune response disorders, e.g. autoimmune disorders and allergic disorders, as well as transplantation procedures. Successful immunotherapy can be aided by increasing the quantity of the regulatory T cells.

The invention is directed to a method for producing regulatory T cells and methods of using the regulatory T cells, especially in the treatment of autoimmune disorders and allergic disorders.

Thus, one aspect, a method for generating a purified regulatory T cell composition having a $CD4^+CD25^+Foxp3^+$ phenotype from naive T cells having $CD4^+CD45RA^+RO^- CD11a^{lo}CD27^+$ phenotype is provided. The method comprises the steps of: stimulating the T cell receptor on the naive T cells and stimulating ICAM-1 on the naive T cells to cause the naive T cells to differentiate into a first composition containing regulatory T cells; and then substantially separating the regulatory T cells from the first composition to form a purified regulatory T cell composition. The regulatory T cells are preferably further proliferated. The regulatory T cells may then be infused into the patient who is suffering from an autoimmune disorder or allergic disorder.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 1 shows that $CD25^-Foxp3^+$ regulatory T cells were induced following co-stimulation of naive $CD4^+$ T cells through ICAM-1.

FIG. 3 shows $CD4^+CD25^+$ cells induced after co-stimulation through ICAM-1 suppressed responder cell proliferation. Human naive $CD4^+$ T cells were stimulated with immobilized anti-CD3 plus anti-ICAM-1 antibodies. After 10 days of stimulation, the $CD4^+CD25^+$ and $CD4^+CD25^-$ populations were each purified using magnetic separation kits. Blood was drawn from the same individual and total T cells were purified using a magnetic separation kit. The newly isolated total T cells (responder cells) were labeled with CFSE. The $CD4^+CD25^+$ cells that had been induced in culture (regulatory T cells) were labeled with PKH26 dye and added to the responder cells at regulatory T cell: responder ratios of 1:1, 1:2, or 1:4. All cells were subsequently exposed to stimulation with plate-bound anti-CD3 plus anti-CD28 antibodies, and the ability of the regulatory T cells to inhibit T cell proliferation was measured using a CFSE dilution assay.

DETAILED DESCRIPTION OF PREFERRED EMBODIMENT

Figure 1A:
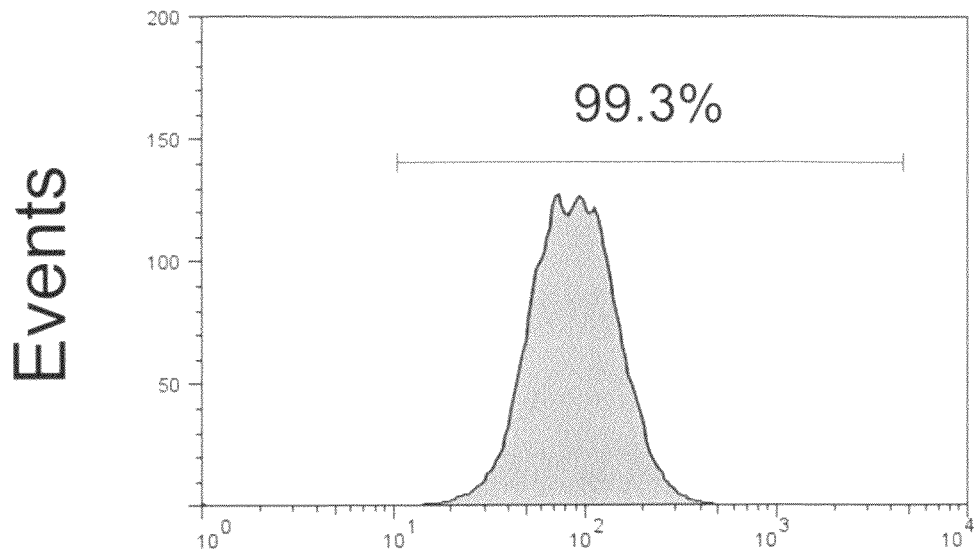
FIG. 1(A) shows that purified human naive $CD4^+$ T cells were $CD45RA^+$ (left panel 99.3%) and $CD11a^{lo}CD27^+$ (right panel 97.3%).
Figure 1A:
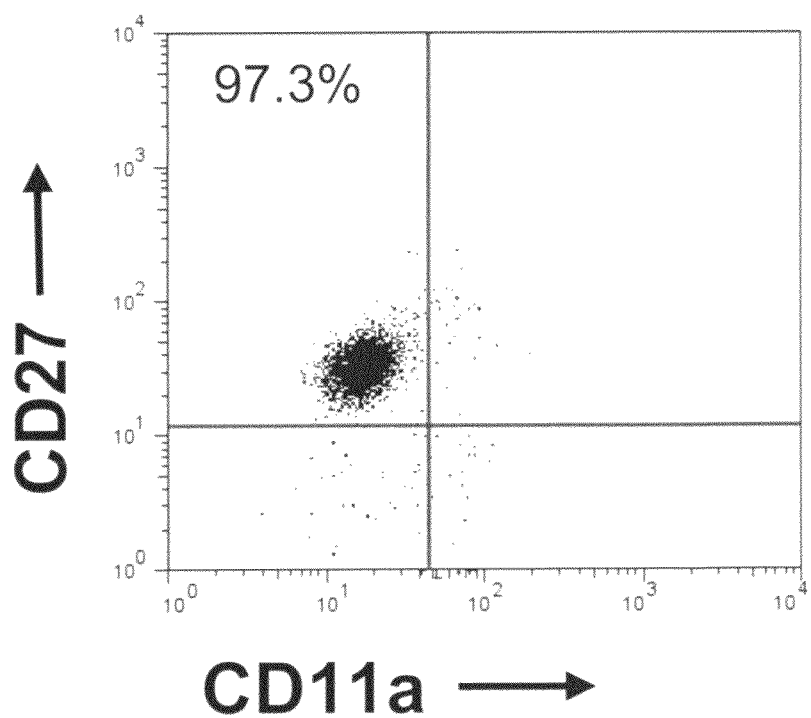
Figure 1B:
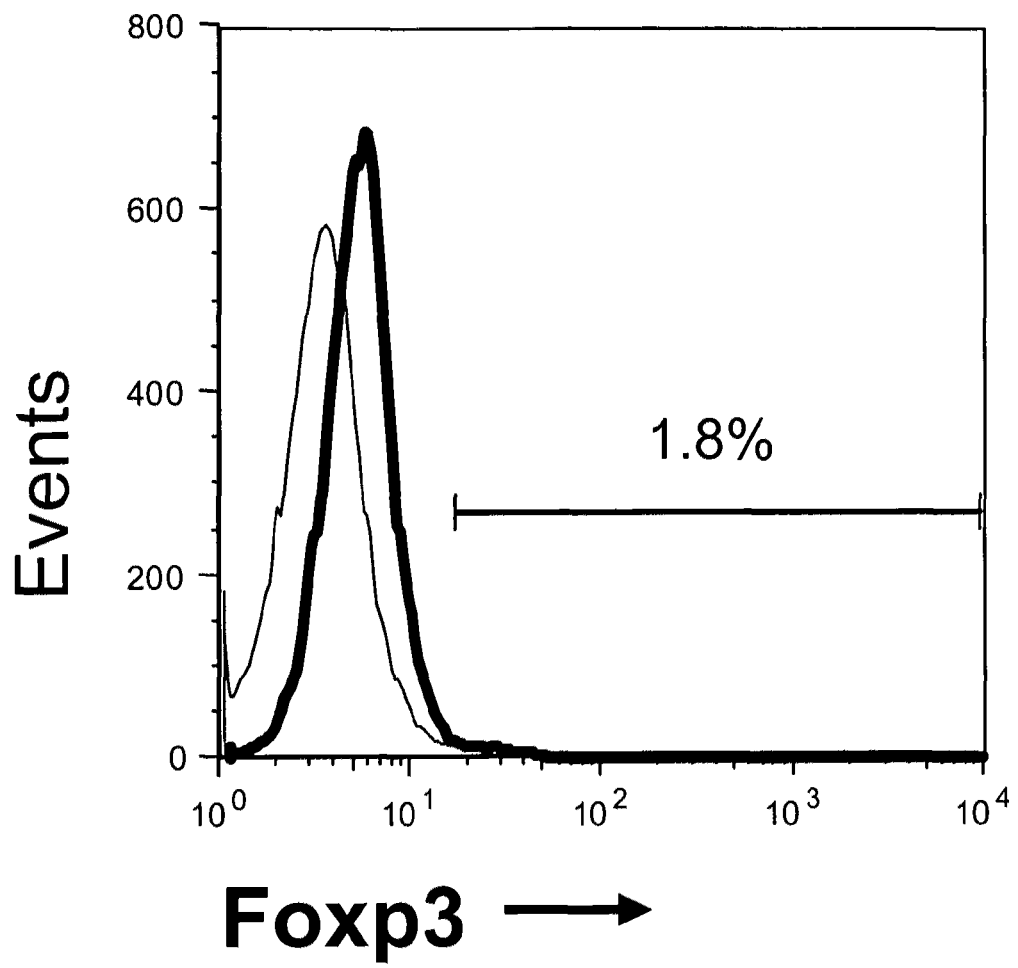
FIG. 1(B) shows that the naïve $CD4^+$ T cell population was greater than 98% $Foxp3^-$. About 1.8% of the starting naïve $CD4^+$ T cells were $Foxp3^{lo}$.

The present invention is directed to a method of promoting the differentiation of naive T cells into regulatory T cells. In one aspect, a population of naive T cells is stimulated through TCR (CD3) and also is stimulated through ICAM. The regulatory T cells are preferably substantially separated from the other cells to form a purified regulatory T cell population.

Stimulation through TCR on the naive T cell is accomplished using a suitable activator. The TCR/CD3 activator is usually selected from an antibody or ligand for TCR/CD3, such as an anti-CD3 or anti-TCR antibody. Although a number of anti-CD3 monoclonal antibodies are commercially available, OKT3 prepared from hybridoma cells obtained from the American Type Culture Collection or monoclonal antibodies, such as G19-4, are preferred. The TCR (CD3) may also be stimulated using antigen-specific activators, such as an MHC-peptide complex. The peptide is typically an autoimmune disorder associated peptide, such as a diabetes-associated autoantigen peptide wherein suitable diabetes-associated autoantigens include glutamic acid decarboxylase ("GAD"), an islet cell autoantigen ("ICA") and insulin, wherein combinations of such peptides may also be used. Other peptides are those derived from myelin proteolipid protein ("PLP"), myelin oligodendrocyte glycoprotein ("MOG"), and oligodendrocyte-specific protein ("OSP"). Suitable stimulating agents (e.g., MHC class II molecule/peptide complexes) are described in Bluestone et al., U.S. Published Patent Application No. 2005/0186027, which is incorporated by reference.

Stimulation of ICAM-1 on the naive T cell is preferably accomplished using an anti-ICAM antibody. ICAM-1 may also be stimulated using small molecule ligands, LFA-1, or other peptides such as those derived from LFA-1. In another aspect, eukaryotic cells stably expressing LFA and membrane anti-CD3 may used to stimulate the T-cells.

In one aspect, the TCR-stimulating agents and ICAM-stimulating agents may be conjugated to each other. For example, a fragment of the anti-CD3 antibody capable of stimulating the TCR may be linked to the fragment of the anti-ICAM-1 antibody capable of stimulating the ICAM-1 using a suitable linker. In general, the techniques described in June et al., U.S. Published Application No. 2006/0205069 entitled "Compositions Comprising a First Agent which Provides a Preliminary Activation Signal to T-Cells and a Second Agent which Stimulates an Accessory Molecule on the Surface of T-Cells," which is incorporated by reference.

In still another aspect, the TCR-stimulating agents and/or ICAM-stimulating agent may be in soluble form or immobilized on a solid support, such as a bead or tissue culture dish. See June, et al., U.S. Pat. Nos. 5,858,358; 6,352,694; 6,534,055; 6,905,681 entitled "Methods for Selectively Stimulating Proliferation of T cells"; June et al., WO 99/953823, which are incorporated by reference. In one embodiment, the two stimulating agents are coupled to the same solid phase surface, such as a bead. The solid phase surface can be plastic, glass, or any other suitable material. Paramagnetic beads are preferred, and are typically in the 1-20 micron range. For example, an antibody such as OKT3 may be placed in 0.05M borate buffer, pH 9.5 and added to tosyl activated magnetic immunobeads (Dynal Inc., Great Neck, N.Y.) according to the manufacturer's instructions. After 24 hours incubation at 22° C., the beads are collected and washed extensively. It is not mandatory that immunomagnetic beads be used, as other methods are also satisfactory. Such techniques are generally described in June et al., U.S. Published Patent Application No. 2006/0205069 entitled "Compositions comprising a first agent which provides a primary activation signal to T cells and a second agent which stimulates an accessory molecule on the surface of T cells"; Porter et al., *A phase I trial of donor lymphocyte infusions expanded and activated ex vivo via CD3/CD28 co-stimulation*, Blood. February 15, 107(4):1325-31 (2006), which are incorporated by reference.

The regulatory T cells are then substantially separated from the population of cells to form a purified regulatory T cell composition. Techniques for affinity separation may include magnetic separation, using antibody-coated magnetic beads, affinity chromatography, cytotoxic agents joined to a monoconal antibody or used in conjunction with a monoclonal antibody, e.g. complement and cytotoxins, and "panning" with antibody attached to a solid matrix, e.g., plate, or other convenient technique. In a preferred aspect, regulatory T cells can be separated by targeting for selection of cell surface markers expressed by regulatory T cells and separating using automated cell sorting, such as fluorescence-activated cell sorting ("FACS"), solid-phase magnetic beads, etc. Positive selection may be combined with negative selection against T cells comprising surface makers specific to non-regulatory T cell types. In a preferred aspect, regulatory T cells will be separated from other cells by removing all cells that express CD127 since CD127 is down regulated in regulatory T cells.

In an exemplary aspect, the naïve human CD4+ cells are first purified using negative selection to remove CD8+ T cells and effector memory T cells (CD54R0), B cells (CD19), macrophages, natural killer cells, and neutrophils. Next, the naïve T cells are differentiated into regulatory T cell by stimulation through TCR and ICAM-1. The non-differentiated T cells will be removed by separating cells that express CD127. Thus, the remaining population will comprise pure regulatory T cells.

In another aspect, the regulatory T cells may be selected against dead cells by employing dyes associated with dead cells (e.g., propidium iodide, ethidium monoazaide). Any technique may be employed which is not unduly detrimental to the viability of the selected cells.

When cell sorting is used, the regulatory T cells may be collected in any appropriate medium that maintains the viability of the cells, usually having a cushion of serum at the bottom of the collection tube. Various media are commercially available and may be used according to the nature of the cells, including Dulbecco's Modified Eagle Medium ("dMEM"), Hank's Basic salt Solution ("HBSS"), Dulbecco's phosphate buffered saline ("dPBS"), RPMI, Iscove's medium, etc., frequently supplemented with fetal calf serum.

In particular, embodiments, at least 75%, 85%, 90%, 95%, or 98% of the cells of the resulting composition are regulatory T cells.

In another aspect, the regulatory T cell compositions may be optionally expanded or proliferated. In particular embodiments, the expanding agent is a cytokine, such as an interleukin (e.g, IL-10). The regulatory T cells are preferably expanded at least 2-fold, and more preferably at least 10, 50, 100, 200, 300, 500, and 800-fold.

The purified regulatory T cells compositions preferably contain a clinically relevant number or population of regulatory T cells. Typically, this is about $10^9$ cells, and is preferably more than $10^{10}$ cells. The number of cells will depend upon the ultimate use for which the composition is intended. The clinically relevant number of cells can be apportioned into multiple infusions that cumulatively equal or exceed $10^9$ or $10^{10}$ cells.

The substantially purified regulatory T cell population may be used immediately. Cells can also be frozen at liquid nitrogen temperatures and stored for long periods of time, being thawed and capable of being reused. The cells may be stored, for example, in DMSO and/or FCS, in combination with medium, glucose, etc. Once thawed, the cells may be expanded by use of growth factors, antigen-stimulation, cytokines dendritic cells, etc.

Uses of T-Regulatory Cells

The regulatory T cell compositions of the present invention are useful for suppression of immune function in a patient. In particular, autologous cells may be used for isolation, modification in vitro, and subsequent administration or re-implantation to the patient.

A therapeutically effective amount of regulatory T cells can be administered with a pharmaceutically acceptable carrier. Administration routes may include any suitable means, including, but are typically intravascularly (intravenously or intra-arterially). The preferred administration route is by IV infusion. The particular mode selected will depend upon the particular treatment. Typically, about $10^9$-$10^{11}$ cells can be administered in a volume of a 50 ml to 1 liter, 50 ml to 250 ml, 50 ml to 150, and typically 100 ml. The volume will depend upon the disorder treated and the route of administration. The cells can be administered in a single dose or in several doses over selected time intervals in order to titrate the dose.

In the case of bone marrow or organ transplantation, the regulatory T cells may be alloactivated using the recipient cells. It will be appreciated that the most convenient time to administer the alloactivated cells to prevent HVGD in a transplant patient is during the time of surgery so preparation of the regulatory T cells should occur in advance of surgery. To keep the cells at the site until completion of the surgical procedure, it is convenient to administer the cells in a pharmaceutically acceptable carrier, such as an artificial gel, or in clotted plasma, or by utilizing any other known controlled release mechanism.

In one aspect, the invention is directed to a method of modulating an aberrant immune response in a subject, such as an autoimmune disorder or an allergy, by administering the regulatory T cells generated by co-stimulation through both ICAM-1 and the TCR. The method comprises (a) obtaining a population of naive T cells from the subject; (b) producing regulatory T cell from the naive T cells; and (c) introducing the composition into the subject to modulate the aberrant immune response or allergy in the subject. The subject usually suffers from an autoimmune disorder or an allergic response, the regulatory T cells are used to treat the autoimmune disorder or allergic disorder. In one embodiment, the subject is an animal model of an autoimmune disorder or allergic disorder. In another embodiment, the subject is a human afflicted with an autoimmune disorder or allergic disorder.

The regulatory T cells produced and optionally expanded regulatory T cells as disclosed herein is effective to suppress a wide variety of autoimmune disorders, including but not limited to, Addison's disease, Alopecia universalis, ankylosing spondylitisis, antiphospholipid antibody syndrome, aplastic anemia, asthma, autoimmune hepatitis autoimmune infertility, autoimmune thyroiditis, autoimmune neutropenia, Behcet's disease, bullous pemphigoid, Chagas' disease, cirrhosis, Cocliac disease, colitis, Crohn's disease, Chronic fatigue syndrome, chronic active hepatitis, dense deposit disease, discoid lupus, degenerative heart disease (e.g. Ziad Mallat, et al., *Induction of a Regulatory T cell Type 1 Response Reduces the Development of Atherosclerosis in Apolipoprotein EBKnockout Mice*, Circulation September 9, 108(10): 1232-7 (2003)), dermatitis, insulin-dependent diabetes mellitus, dysautonomia, endometriosis, glomerulonephritis, Goodpasture's disease, Graves' disease, graft-versus-host disease (GVHD), Graves' disease, Guillain-Barre syndrome, Hashimoto's disease, hemolytic anemia, Hidradenitis suppurativa, idiopathic thrombocytopenia purpura, inflammatory bowel disease ("IBD"), insulin dependent diabetes mellitus, interstitial cystitis, mixed connective tissue disease, multiple sclerosis ("MS"), myasthenia gravis, neuromyotonia, opsoclonus myoclonus syndrome, optic neuritis, Ord's thyroiditis, pemphigus vulgaris, pernicious anemia, polyarthritis, polymyositis, primary biliary cirrhosis, psoriasis, Reiter's syndrome, rheumatoid arthritis ("RA"), sarcoidosis, scleroderma, Sjogren's syndrome, systemic lupus erythematosus, Takayasu's arteritis, temporal arteritis, thrombocytopenia purpura, ulcerative colitis, vitiligo, vulvodynia, warm autoimmune hemolytic anemia, or Wegener's granulomatosis, etc., as demonstrated in documented animal models and human clinical trials. There are numerous, established animal models for using T cell epitopes of autoantigens to induce tolerance, including multiple sclerosis (EAF: experimental autoimmune encephalomyelitis), myasthenia gravis (EMG: experimental myasthenia gravis) and neuritis (EAN: experimental autoimmune neuritis). Such regulatory T cell uses are generally described in Bluestone et al., U.S. Published Patent Application No. 2005/0186207 entitled "Regulatory Cells Suppress Autoimmunity"; Horwitz, U.S. Pat. No. 6,797,267 entitled "Use of Cytokines and Mitogens to Inhibit Pathological Immune Responses"; Barratt et al., U.S. Pat. No. 6,670, 146 entitled "Regulatory T cells; Methods"; Norment et al., U.S. Published Patent Application No. 2006/0063256 entitled "Human Regulatory T cells and Uses Thereof", Blazar et al., U.S. Published patent Application No. 2005/019386 entitled "Regulatory T cells and Their uses in Immunotherapy and Suppression of Autoimmune responses," which are incorporated by reference in their entirety.

The regulatory T cells produced and optionally expanded regulatory T cells as disclosed herein is effective to suppress a wide variety of allergic disorders including, but are not limited to, allergic conjunctivitis, allergic rhinitis, allergic contact dermatitis, alopecia universalis, anaphylactoid purpura, asthma, atopic dermatitis, dermatitis herpetiformis, erythema elevatum diutinum, erythema marginatum, erythema multiforme; erythema nodosum, allergic granulomatosis, granuloma annulare, granlocytopenia, hypersensitivity pncumonitis, keratitis, neplirotic syndrome, overlap syndrome, pigcon breeder's disease, pollinosis, idiopathic polyneuritis, urticaria, uveitis, juvenile dermatomyositisitis, and vitiligo.

In one aspect, the regulatory T cells are introduced into the subject treat an autoimmune disorder or allergic disorder. For example, the subject may be afflicted with a disease characterized by having an ongoing or recurring autoimmune reaction or allergic reaction. In particular, embodiments, the modulating comprises inhibiting the autoimmune reaction or allergic reaction. Regulatory T cells may also serve as a "Trojan Horse" to deliver suppressive or other biologic factors to sites of inflammation, such as IL-4 (Yamamoto et al., *The Activity of Immunoregulatory T cells Mediating Active Tolerance is Potentiated in Nonobese Diabetic Mice by an IL-4-Based Retroviral Gene Therapy*[1], J. Immunol. 166:4973-80, (2001)), stem cell growth factors, angiogenesis regulators, genetic deficiencies, etc. For example, overexpression of Foxp3 has been shown to transform otherwise pathogenic T cells into regulatory T cells (Jaeckel et al., *Antigen-Specific FoxP3-Transduced T cells Can Control Established Type I Diabetes*, Diabetes, Dec. 10 (2004) [Epub]), and polyclonally expanded regulatory T cells can be transduced with genes encoding an antigen-specific TCR plus Foxp3 to generate potent antigen-specific regulatory T cells in very high numbers and efficiency (Mekala, et al., *Immunotherapy of autoimmune encephalomyelitis with re-directed $CD4^+CD25^+$ T-lymphocytes*, Blood, Nov. 4; (2004) [Epub]). Thus, these antigen-specific approaches decrease the requirement for high cell numbers while maximizing regulatory T cell specificity and function.

Regulatory T cells are particularly indicated in infectious diseases in which the pathogenicity of the infections is not a result of the cytopathic effects of the pathogen but rather the tissue damage caused by the immunoinflammatory response to the infectious agent. In diseases, such as hepatitis B or C or HSV-induced corneal inflammation, regulatory T cell therapy provides a unique opportunity to control viral-induced immunoinflammatory disease (Suvas et al., *$CD4^+CD25^+$ Regulatory T cells Control the Severity Of Viral Immunoinflammatory Lesions*[1], J. Immunol. 172: 4123-4132, (2004)). Viruses, such as Coxsackie, are known to cause pancreatitis and have been associated with the development of Type 1 Diabetes. Thus, regulatory T cells that target expressed viral antigens can be used to suppress local tissue damage caused by the infection and reduce the inflammation that incites autoimmune disorder development.

The subject methods find use in the treatment of a variety of different conditions and transplant situations in which the modulation of an aberrant immune response in a patient is desired.

DEFINITIONS

As used herein, the singular forms "a," "an," and "the" include plural referents unless the context clearly dictates otherwise. Thus, for example, reference to "a pharmaceutical carrier" includes mixtures of two or more such carriers, and the like.

As used herein, the term "aberrant immune response" embraces the failure of a subject's immune system to distinguish self from non-self or the failure to respond to foreign antigens. The term also embraces hyperimmune responses to foreign antigens as in the case of allergic disorders. Thus, the response is present in both autoimmune disorders and allergic disorders. Aberrant immune responses include, but are not limited to, tissue injury and inflammation caused by the production of antibodies to an organism's own tissue, impaired production of cytokines and tissue damage caused by cytotoxic or non-cytotoxic mechanisms of action. In other words, aberrant immune responses are inappropriately regulated immune responses that lead to patient symptoms. In general, autoimmune responses occur when the immune system of a subject recognizes self-antigens as foreign, leading to the production of self-reactive effector immune cells. Self-reactive effector immune cells include cells from a variety of lineages, including, but not limited to, cytotoxic T cells, helper T cells, and B cells. While the precise mechanisms differ, the presence of autoreactive effector immune cells in a patient suffering from an autoimmune disorder leads to the destruction of tissues and cells of the patient, resulting in pathologic symptoms. Similarly, the presence of cells that undergo a hypersensitive reaction to foreign antigens to which normal individuals respond in a more restrain manner is indicative of hypersensitivity (allergy). Examples include, but are not limited to, food allergies, hay fever, and allergic asthma. Numerous assays for determining the presence of such cells in a patient, and therefore the presence of an autoimmune disorder, such as an antigen specific autoimmune disorder in a patient, or an allergic disorder, are known to those of skill in the art and readily employed in the subject methods. Assays of interest include, but are not limited to, those described in: Autoimmunity, September-November 2003; 36(6-7) 361-366; McMillan, *Antiplatelet Antibodies in Chronic Adult Immune Thrombocytopenic Purpura: Assays and Epitopes*, J. Pediatr. Hematol. Oncol. December 25 Suppl 1:S57-61 (2003); Proteomics November; 3(11) 2077-2084 (2003); Autoimmun. Rev. January 2(1) 43-49 (2003).

As used herein, the term "antibody" embraces polyclonal and monoclonal antibodies, chimeric antibodies, haptens and antibody fragments, and molecules which are antibody equivalents in that they specifically bind to an epitope on the antigen of interest (e.g. counter receptors for the TCR/CD3 complex and ICAM-1). The term "antibody" includes polyclonal and monoclonal antibodies of any isotype (IgA, IgG, IgE, IgD, IgM), or an antigen-binding portion thereof, including, but not limited to, F(ab) and Fv fragments such as sc Fv, single chain antibodies, chimeric antibodies, humanized antibodies, and a Fab expression library. When used to stimulate a T cell, antibodies can also be immobilized for instance on a solid phase surface, such as a particle as discussed above.

As used herein, the term "antigen" embraces any molecule capable of generating an immune response. In the context of autoimmune disorders, the antigen is a self-antigen.

As used herein, the term "antigen-specific regulatory T cells" refers to regulatory T cells which were activated in the presence of an antigen and which express the cell surface markers $CD4^+$ and $CD25^+$, which and preferably express Foxp3 protein as measured by a Western blot, flow cytometry, and/or Foxp3 mRNA transcript as measured in vitro. In an in vitro proliferation assay, after re-exposure to the cognate antigen used for induction, antigen-specific regulatory T cells are capable of actively suppressing the proliferation of freshly isolated $CD4^+CD25^-$ T cell responder cells which have been stimulated in culture with an activating signal.

As used herein, the term "cell" embraces a single cell as well as a plurality or population of cells.

As used herein, "immune response" embraces a patient response to foreign or self antigens. The term includes cell mediated, humoral, or inflammatory responses.

As used herein, "inappropriately regulated" embraces the state of being inappropriately induced, inappropriately suppressed and/or non-responsiveness.

As used herein, the term "naive cells" embraces T cells that express the $CD4^+CD45RA^+RO^-CD11a^{lo}CD27^+$ phenotype. Naive cells are undifferentiated T cells and have not been exposed to their cognate antigen.

As used herein, "patient" or "subject" means a mammalian subject to be treated, with human patients being preferred. In some cases, the methods of the invention find use in experimental animals, in veterinary application, and in the development of animal models for disease, including, but not limited to, dogs, cats, pigs, horses, cattle, chimpanzees, monkeys, rodents including mice, rats, and hamsters, and primates.

As used herein, "proliferation" or "expansion" refers to the ability of a cell or population of cells to increase in number.

As used herein, a composition containing a "purified cell population" or "purified cell composition" means that at least 30%, 50%, 60%, typically at least 70%, and more preferably 80%, 90%, 95%, 98%, or 99% of the cells in the composition are of the identified type.

As used herein, the term "regulatory T cell" embraces T cells that express $CD4^+CD25^+$ phenotype. Most preferably, the regulatory T cells also express the Foxp3 transcription factor as measured by a flow cytometry, Western blot and/or Foxp3 mRNA transcript as measured in vitro and are thus express the $CD4^+CD25^+$ Foxp3$^+$ phenotype.

As the term is used herein, "substantially separated from" or "substantially separating" refers to the characteristic of a population of first substances being removed from the proximity of a population of second substances, wherein the population of first substances is not necessarily devoid of the second substance, and the population of second substances is not necessarily devoid of the first substance. However, a population of first substances that is "substantially separated from" a population of second substances has a measurably lower content of second substances as compared to the non-separated mixture of first and second substances. In one aspect, at least 30%, 50%, 60%, 70%, 80%, 90%, 95%, 98%, or 99% of the second substance is removed from the first substance.

The terms "suppression," "inhibition" and "prevention" are used herein in accordance with accepted definitions i.e., "suppression" results when an ongoing immune response is blocked or significantly reduced as compared with the level of immune response that results absent treatment by the present invention. Similarly, "inhibition" refers to blocking the occurrence of an immune response or significantly reducing such response as compared with the level of immune response that results absent treatment by the present invention. When administered prophylactically, such blockage may be complete so that no targeted immune response occurs, typically referred to as a "prevention" with regard to completely blocking the immune response before onset; or in the present invention, the treatment may advantageously reduce the effect as compared to the normal untreated state, typically referred to as suppression or inhibition.

As used herein, "therapeutically effective" refers to an amount of cells that is sufficient to treat or ameliorate, or in some manner reduce the symptoms associated with a disease or disorder. When used with reference to a method, the method is sufficiently effective to treat or ameliorate, or in some manner reduce the symptoms associated with a disease or disorder. For example, in bone marrow transplant patients experiencing the onset of GVHD, or those that are susceptible to GVHD, an effective amount is that amount which is sufficient to block or prevent its onset; or if GVHD pathology has begun, to palliate, ameliorate, stabilize, reverse or slow progression of the disease, or otherwise reduce pathological consequences of the disease. In any case, an effective amount may be given in single or divided doses.

As used herein, the term "treatment" embraces at least an amelioration of the symptoms associated with the aberrant immune response in the patient is achieved, where amelioration is used in a broad sense to refer to at least a reduction in the magnitude of a parameter, e.g. symptom, associated with the condition being treated. As such, "treatment" also includes situations where the disease, disorder, or pathological condition, or at least symptoms associated therewith, are completely inhibited, e.g. prevented from happening, or stopped, e.g. terminated, such that the patient no longer suffers from the condition, or at least the symptoms that characterize the condition.

Materials and Methods

Cell Purification

Human naive $CD4^+$ T cells were isolated from peripheral blood of healthy donors using Ficoll-Paque PLUS (GE Healthcare, Piscataway, N.J.) density gradient centrifugation followed by negative selection using Human Naive $CD4^+$ T cell Enrichment Kits (StemCell Technologies, Vancouver, BC) as previously described (Chirathaworn et al., 2002). Naive cells for this study were defined as $CD4^+CD45RA^+CD45RO^-CD11a^{lo}CD27^+$ and routinely had a purity of greater than 97% as determined by flow cytometry. Cells were cultured in complete RPMI 1640 medium (Mediatech, Herndon, Va.) containing 10% FBS (Irvine Scientific, Santa Ana, Calif.), 2 mM L-glutamine, 50 units/mL penicillin, and 50 µg/mL streptomycin (Invitrogen, Carlsbad, Calif.).

Antibodies and Reagents

Hybridomas expressing anti-ICAM-1 (R6.5D6) or anti-CD11a (HB202) were obtained from ATCC (Manassas. Va.) and antibodies were purified from serum-free hybridoma cultures. Anti-CD3 (OKT3) was either purified from serum-free hybridoma culture (ATCC) or was purchased from ebioscience (San Diego, Calif.). The anti-CD3 antibodies from both sources were used with similar results. Anti-CD28 (ANC28.1) purchased from Ancell (Bayport, Minn.) or anti-CD28 (CD28.2) purchased from BD Pharmingen (San Diego, Calif.) were used with similar results. Anti-human Foxp3-FITC and anti-human Foxp3-PE (clone PCH101) were purchased from eBioscience and used with the accompanying Fixation/Permeabilization reagents. Isotype control antibodies for anti-Foxp3 were Rat IgG2a-FITC (eBioscience) and Rat IgG2a-PE (Cattag, Burlingame, Calif.). Anti-CD25-FITC, anti-CD25-TriColor, anti-CD11a-FITC, anti-CD27-PE, anti-CD45RA-TriColor, and anti-CD45RO-TriColor were purchased from Caltag Laboratories. Anti-CD127-PE antibody was purchased from BD Pharmingen. Blocking anti-IL-2 and anti-TGF-β antibodies were purchased from R&D Systems and anti-IL-10 antibody was purchased from BD Pharmingen. Isotype control antibodies were purchased from eBioscience. CFSE (5-(and-6)-carboxyfluorescein diacetate, succinimidyl ester) was purchased from Molecular Probes (Carlsbad, Calif.) and used at 2.5 µM. Flow cytometry was performed using a FACScan (BD, San Jose, Calif.). Data analysis was performed using CellQuest software (BD) and FlowJo software (Tree Star, Inc., Ashland, Oreg.).

Naive CD4+ T Cell Stimulation

Stimulation of human naive CD4+ T cells was performed using plate-bound antibodies. Antibodies in PBS were adhered to tissue-culture treated 96-well plates (Midwest Scientific, St. Louis, Mo.) by incubation at 37° for two hours. Wells were washed three times with PBS to remove unbound antibody. Antibodies were used at the minimum concentrations that resulted in maximum T cell proliferation (data not shown): anti-CD3 (1 µg/mL), anti-ICAM-1 (10 µg/mL), anti-CD11a (10 µg/mL), and anti-CD28 (2 µg/mL). Cells were stimulated at $1.5 \times 10^6$ cells/mL in complete RPMI 1640.

Cytokine ELISA

Cell culture supernatants were collected from stimulated cultures and used after clarification by centrifugation. IL-10 ELISA was performed using Human IL-10 ELISA Ready-Set-Go kits (eBioscience, San Diego, Calif.) or Human IL-10 Quantikine kits (R&D Systems, Minneapolis, Minn.). Plates were analyzed using an Automated Microplate Reader (BioTek, Winooski, Vt.) and DeltaSoft software (BioMetallics Inc, Princeton, N.J.).

Suppression Assay

Naive CD4+ T cells were stimulated for 10 days using anti-CD3 plus anti-ICAM-1 antibodies as described above. On Day 10, the stimulated cells were spun over Ficoll-Paque (GE Healthcare, Piscataway, N.J.) to remove dead cells. The CD4+CD25+ regulatory T cells were separated from the CD4+CD25− cells using CD4+CD25+ regulatory T cell isolation Kits (Miltenyi Biotec, Auburn, Calif.). Also on Day 10, fresh peripheral blood was again obtained from the same donor and second bleed total T cells were isolated using Ficoll-Paque density centrifugation and a Human T cell Enrichment Kit (StemCell Technologies, Vancouver, BC). The cultured CD4+CD25+ regulatory T cells, the cultured CD4+CD25− cells, and an aliquot of second bleed total T cells to be used as a control were each stained with PKH26 dye (Sigma, St. Louis, Mo.) at 2.5 µM concentration. An aliquot of second bleed total T cells to be used as responders was labeled with CFSE (Molecular Probes, Carlsbad, Calif.) at 2.5 µM concentration. Subsequently, the cells were cultured at regulatory T cell (or Control) Cell: Responder Cell ratios of 1:1, 1:2, and 1:4. Cells were stimulated for five days using anti-CD3 plus anti-CD28 antibodies as described above ($3 \times 10^5$ cells/well). Proliferation of the CFSE-labeled responder cell population was assessed using flow cytometry by gating out the PKH26-labeled regulatory T cell or control populations and analyzing proliferation of the CFSE-labeled responder population.

EXAMPLE 1

Co-Stimulation of Naive T Cells Through ICAM-1 Generated T Cells with a Phenotype Characteristic of Regulatory T Cells To analyze the potential function of ICAM-1 in the differentiation of regulatory T cells, human naive CD4+ cells were isolated as shown in FIG. 1(A). These naive CD4+ cells ($3 \times 10^5$ cells/well) were stimulated in 96-well plates coated with immobilized antibodies against CD3 and different co-stimulatory molecules. The treatment groups were as follows: (1) Nonstimulated, (2) anti-CD3 alone, (3) anti-CD3 plus anti-ICAM-1, (4) anti-CD3 plus anti-CD11a (LFA-1), and (5) anti-CD3 plus anti-CD28.

Figure 1C:
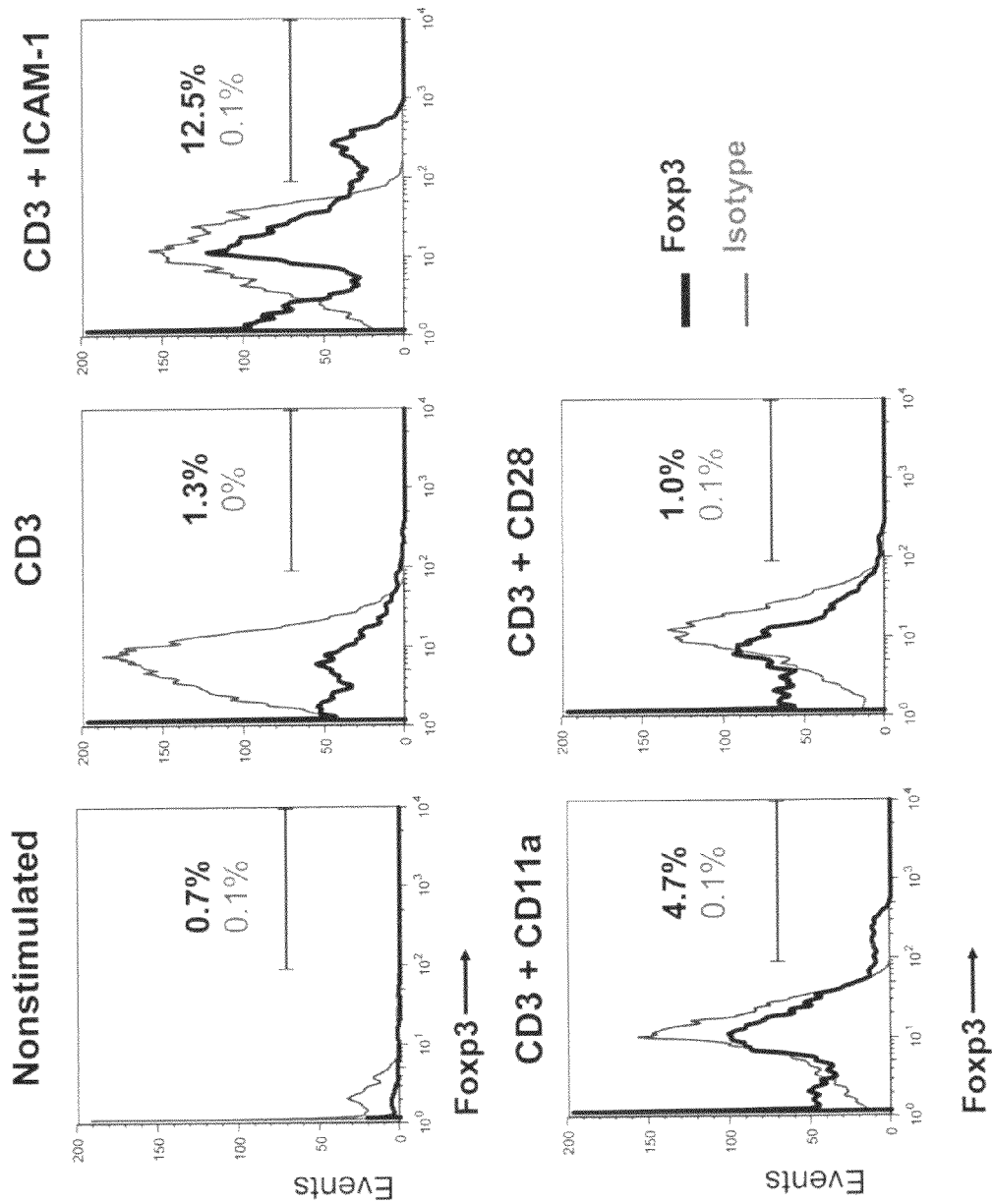
FIG. 1(C) shows the results of naive $CD4^+$ T cells stimulated as indicated for 14 days and then analyzed using flow cytometry. The percentage of $Foxp3^+$ cells is shown in black while the percentage of Isotype $Ab^+$ cells is shown in gray.
Figure 1D:
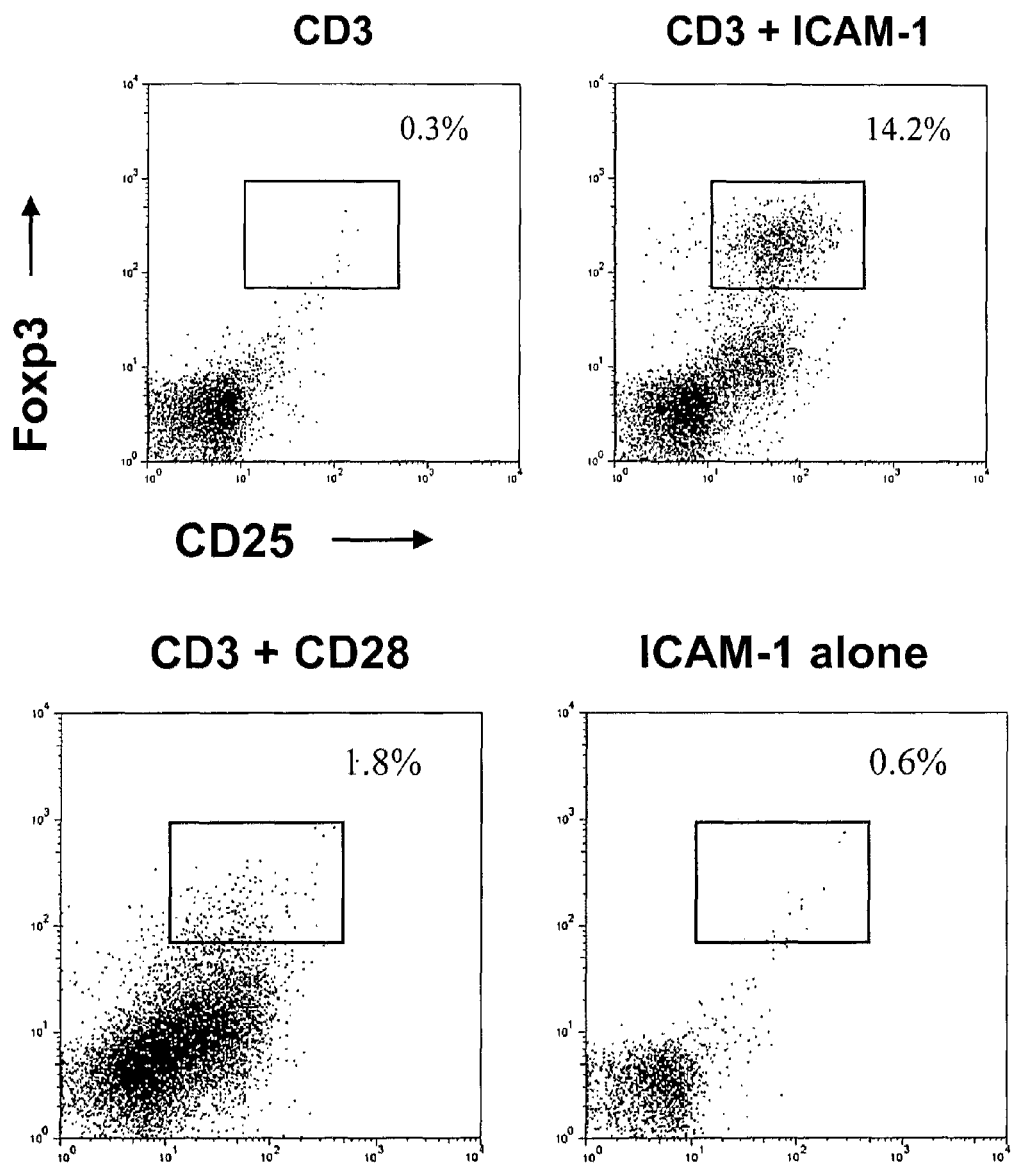
FIG. 1(D) shows naive $CD4^+$ T cells stimulated as indicated for seven days. The percentage of $CD25^+Foxp3^+$ cells is shown for each treatment. The data are representative of more than five experiments.
Figure 1E:
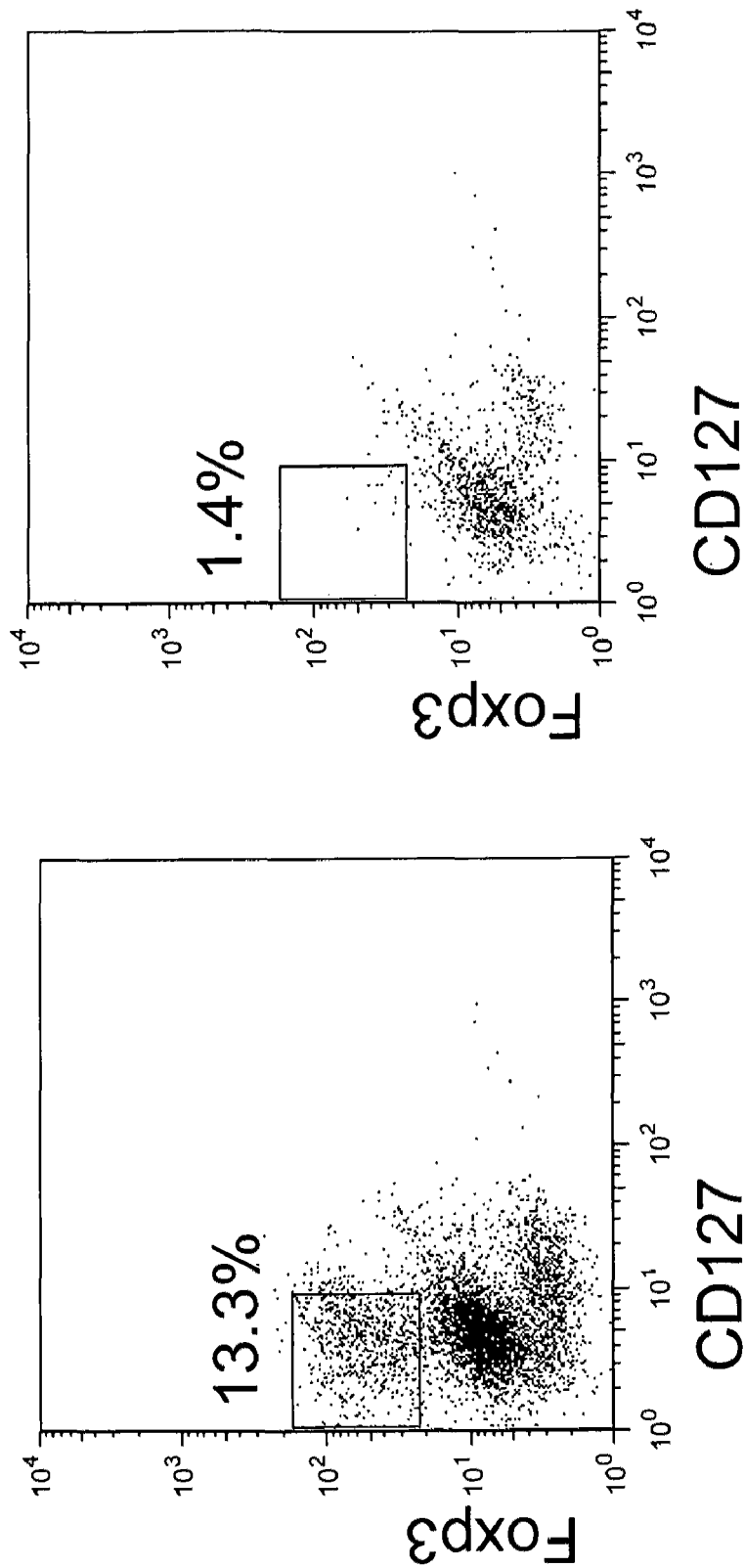
FIG. 1(E) shows that the $Foxp3^+$ population was also $CD127^-$.

The treated cells were then assessed for the presence of Foxp3. After approximately five days of stimulation using anti-CD3 plus anti-ICAM-1, a cellular subset was detected with a regulatory T cell phenotype expressing the intracellular regulatory T cell marker Foxp3 (FIG. 1(C)), the extracellular regulatory T cell marker CD25 (FIG. 1(D)) and CD127 (FIG. 1(E)). There was no observable regulatory T cell population in the CD3 stimulated, or CD3 plus CD28 stimulated samples. However, a small population of regulatory T cells after co-stimulation through CD3 plus CD11a (LFA-1) was observed. In addition, a large subset of cells co-stimulated through CD28 or LFA-1 appeared to express low levels of Foxp3. This may indicate nonspecific Foxp3 antibody binding or may indicate that activation through these markers promotes a slight increase in Foxp3 expression. Stimulation through ICAM-1 alone did not generate a regulatory T cell population.

EXAMPLE 2

Figure 1F:
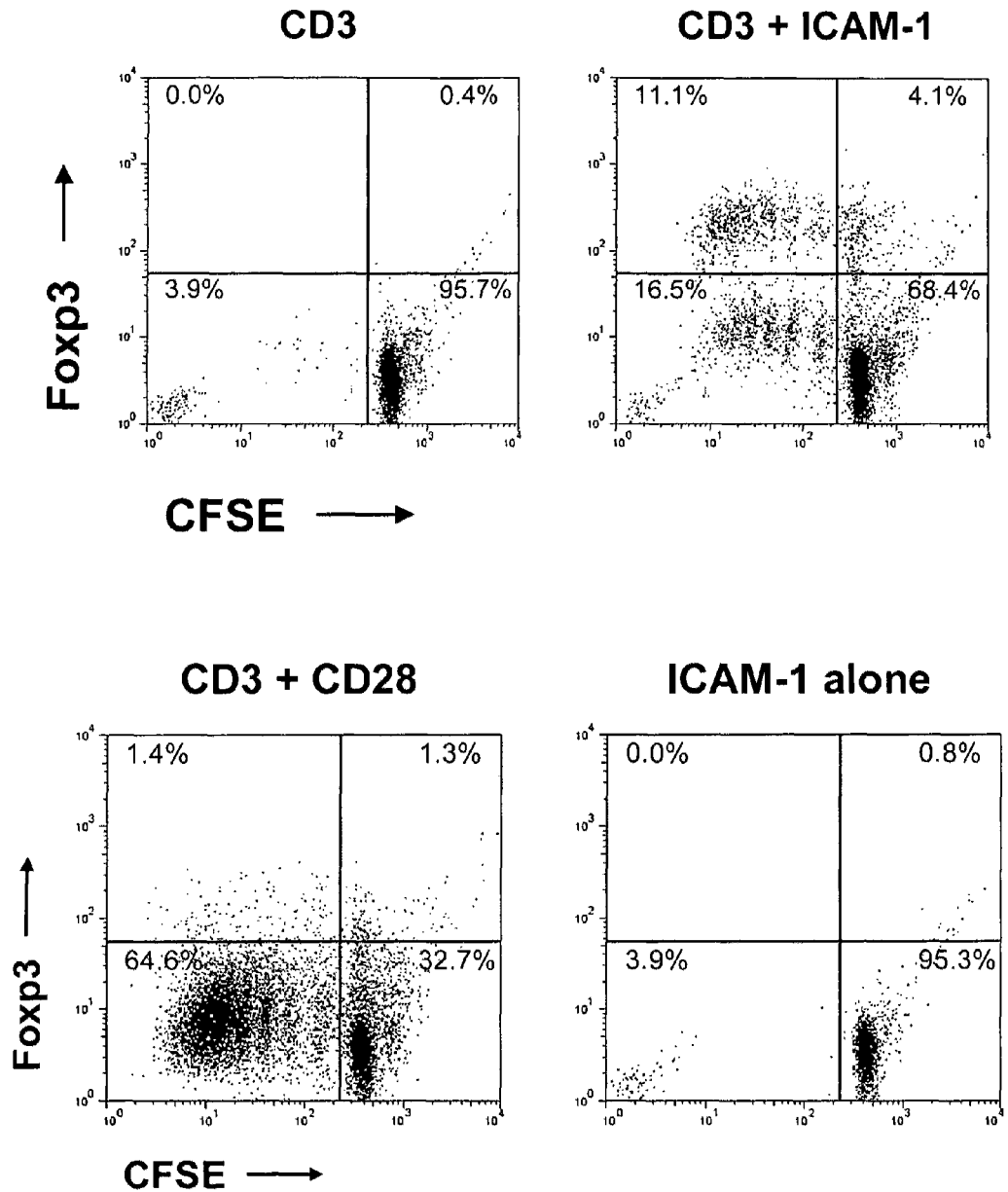
FIG. 1(F) shows naive $CD4^+$ T cells stained with 5-(and-6)-carboxyfluorescein diacetate succinimidyl ester ("CFSE") and stimulated as indicated. After seven days of co-stimulation through ICAM-1, cell division and Foxp3 expression were analyzed. The data are representative of three experiments.
Figure 1G:
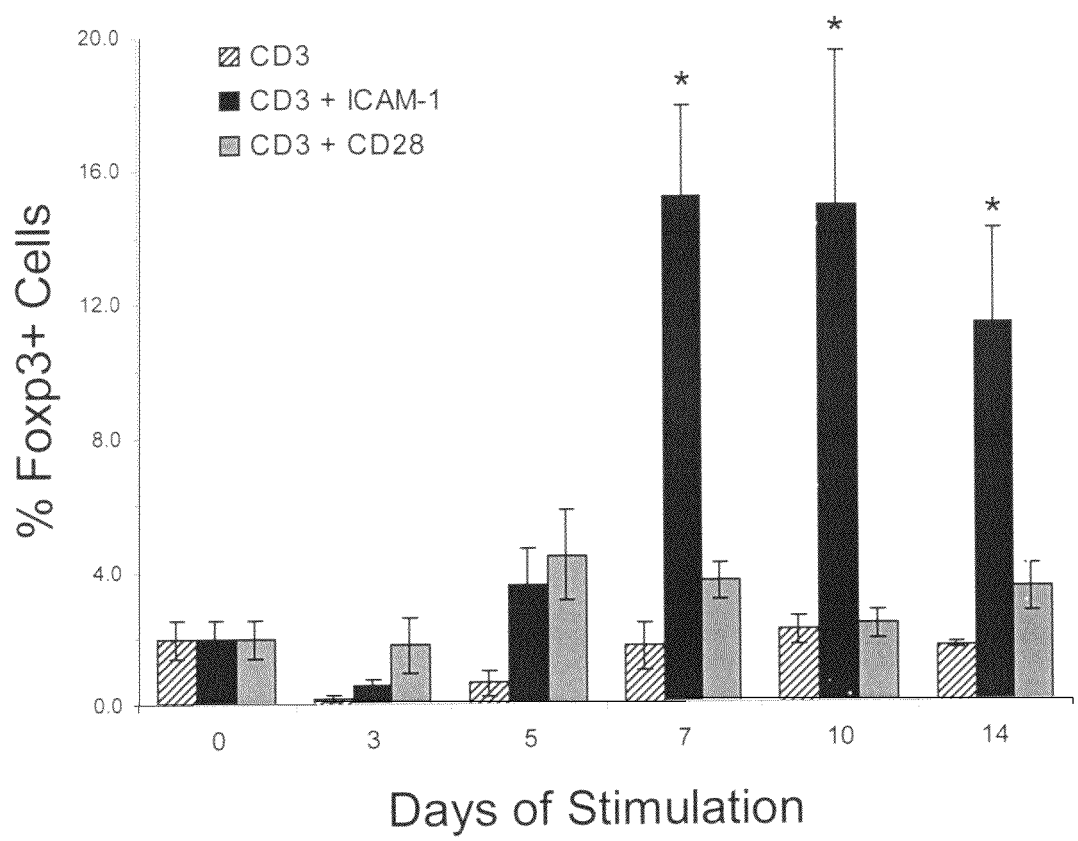
In FIG. 1(G), the kinetics of regulatory T cell induction are presented for cells stimulated through CD3, CD3 plus ICAM-1, and CD3 plus CD28. The mean percentage (%) of $Foxp3^+$ cells in 3-6 separate experiments is shown for each time point. The asterisks indicated a statistically significant difference between the initial percentage of $Foxp3^+$ cells on Day 0 and the percentage of $Foxp3^+$ cells after co-stimulation through ICAM-1 on the indicated days (two-tailed t-Test assuming unequal variances, $p<0.05$).

Co-Stimulation of Naive T Cells Through ICAM-1 Generated Regulatory T Cells That Underwent Proliferation Studies to determine whether regulatory T cells can proliferate in culture have yielded conflicting results. Thus, this example assesses the proliferation of the regulatory T cell population after co-stimulation through ICAM-1 during the differentiation process. Newly purified naive CD4+ T cells were stained with CFSE and stimulated using the indicated treatment regimens (FIG. 1(F)). After seven days of stimulation, the Foxp3+ population included both undivided cells and cells that had undergone cell division. Even though cells proliferated robustly with co-stimulation through CD28, an appreciable population of Foxp3+ cells was not detected with this stimulation condition. When the kinetics of regulatory T cell induction were analyzed, we observed that the percentage of Foxp3+ regulatory T cells was highest at day 7 of stimulation through CD3 plus ICAM-1 (FIG. 1(G)).

EXAMPLE 3

ICAM-1 Co-Stimulation Resulted in Strong IL-10 Production

Figure 2:
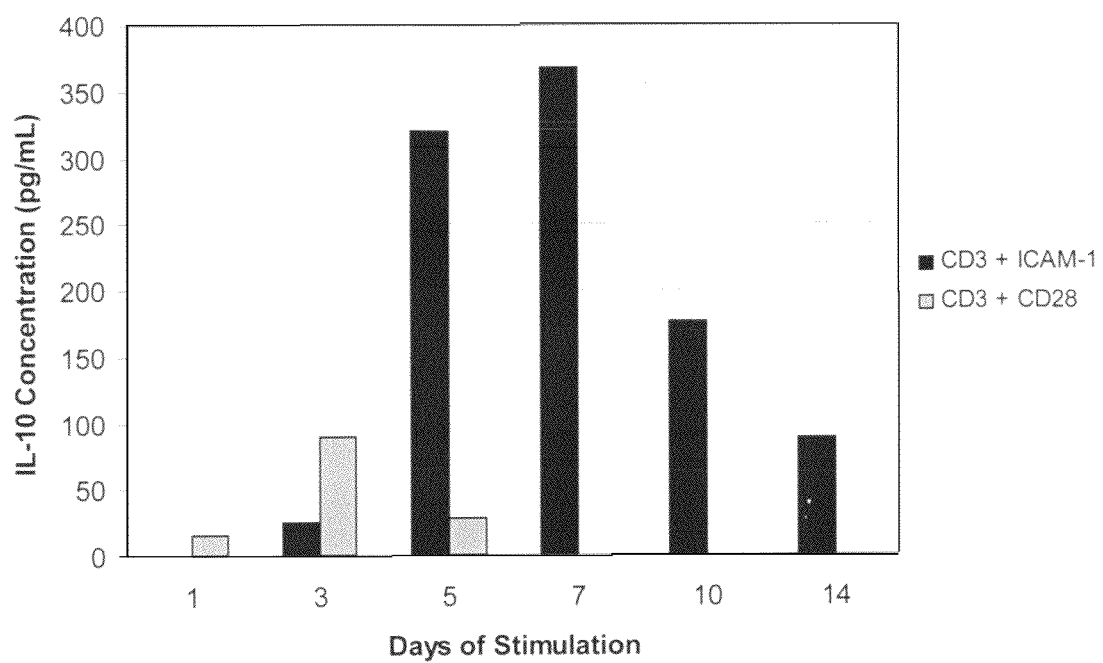
FIG. 2 shows that IL-10 was produced following co-stimulation of naive $CD4^+$ T cells through ICAM-1. Human naive $CD4^+$ T cells were stimulated with anti-CD3 plus anti-ICAM-1 antibodies or anti-CD3 plus anti-CD28 antibodies. Cell culture supernatants were collected at various time points and assayed in duplicate using IL-10 ELISAs. The data are shown as the mean of duplicate samples from one experiment. The data are representative of three experiments.

One mechanism of regulatory T cell suppression is the production of the immunosuppressive cytokine IL-10 which functions to inhibit IL-2 production and proliferation of T cells. Thus, cell culture supernatants from naive CD4+ T cells stimulated through CD3 plus ICAM-1 or through CD3 plus CD28 were collected. IL-10 ELISA detected large amounts of IL-10 in supernatants from cells co-stimulated through ICAM-1 (FIG. 2). Interestingly, the concentration of IL-10 peaked on day 7, which corresponds to the day of the highest regulatory T cell percentage in ICAM-1 co-stimulated cultures (FIG. 1(G)). Small amounts of IL-10 were produced by cells co-stimulated through CD28 on days 1 through 5, but no IL-10 was detected after day 5.

EXAMPLE 4

Co-Stimulation of Naive T Cells Through ICAM-1 Generated T Cells That Were Capable of Suppressing Activation and Proliferation of Other T Cells To verify that the $CD4^+CD25^+Foxp3^+$ population generated after ICAM-1 co-stimulation could function as regulatory T cells, the ability of these cells to suppress the activation and proliferation of other T cells was investigated. Isolated naive $CD4^+$ T cells were stimulated using anti-CD3 plus anti-ICAM-1. After 10 days of stimulation, the stimulated cells were collected and separated into $CD4^+CD25^+$ and $CD4^+CD25^-$ populations. These cells were labeled with a membrane-binding fluorescent dye, PKH26 to allow them to be gated out of the flow cytometry profile. This allowed the analysis of the proliferation of the responder cells only. Also on this day, total T cells were collected from the peripheral blood of the original donor. A group of these total T cells was labeled with PKH26 to use as control cells. The remaining cells were labeled with the intracellular dye CFSE. Thus, the populations of cells used in the suppression assay were: (1) CFSE-labeled Responder T cells (newly isolated), (2) PKH26-labeled Control T cells (newly isolated), (3) PKH26-labeled $CD4^+CD25^+$ regulatory T cells (from stimulated cultures), and (4) PKH26-labeled $CD4^+CD25^-$ cells (from stimulated cultures). The cells were cultured at regulatory T cell (or control) to Responder cell ratios of 1:4, 1:2, and 1:1 and stimulated with anti-CD3 plus anti-CD28 for five days. Proliferation of the CFSE-labeled responder cell population was measured by flow cytometry after gating-out the PKI126-labeled regulatory T cell or control cells.

Figure 3A:
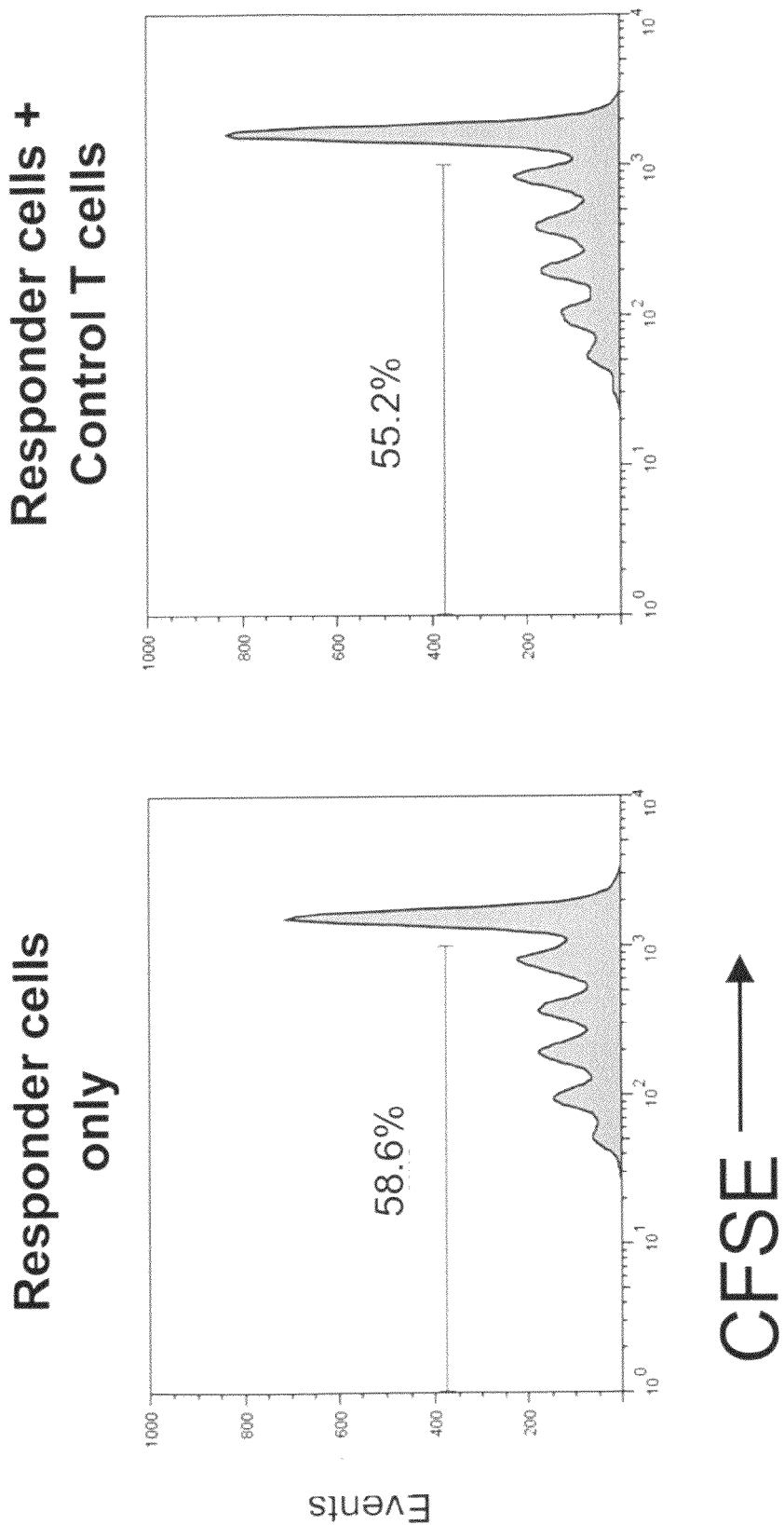
In FIG. 3(A), $CD4^+CD25^+$ regulatory T cells were added at a regulatory T cell: responder ratio of 1:4. As controls, PKH26-labeled total T cells or $CD4^+CD25^-$ cells were added to the responder cells at a 1:4 ratio. The percentage of cells undergoing cell division is shown for each treatment. The data are representative of three experiments.
Figure 3A:
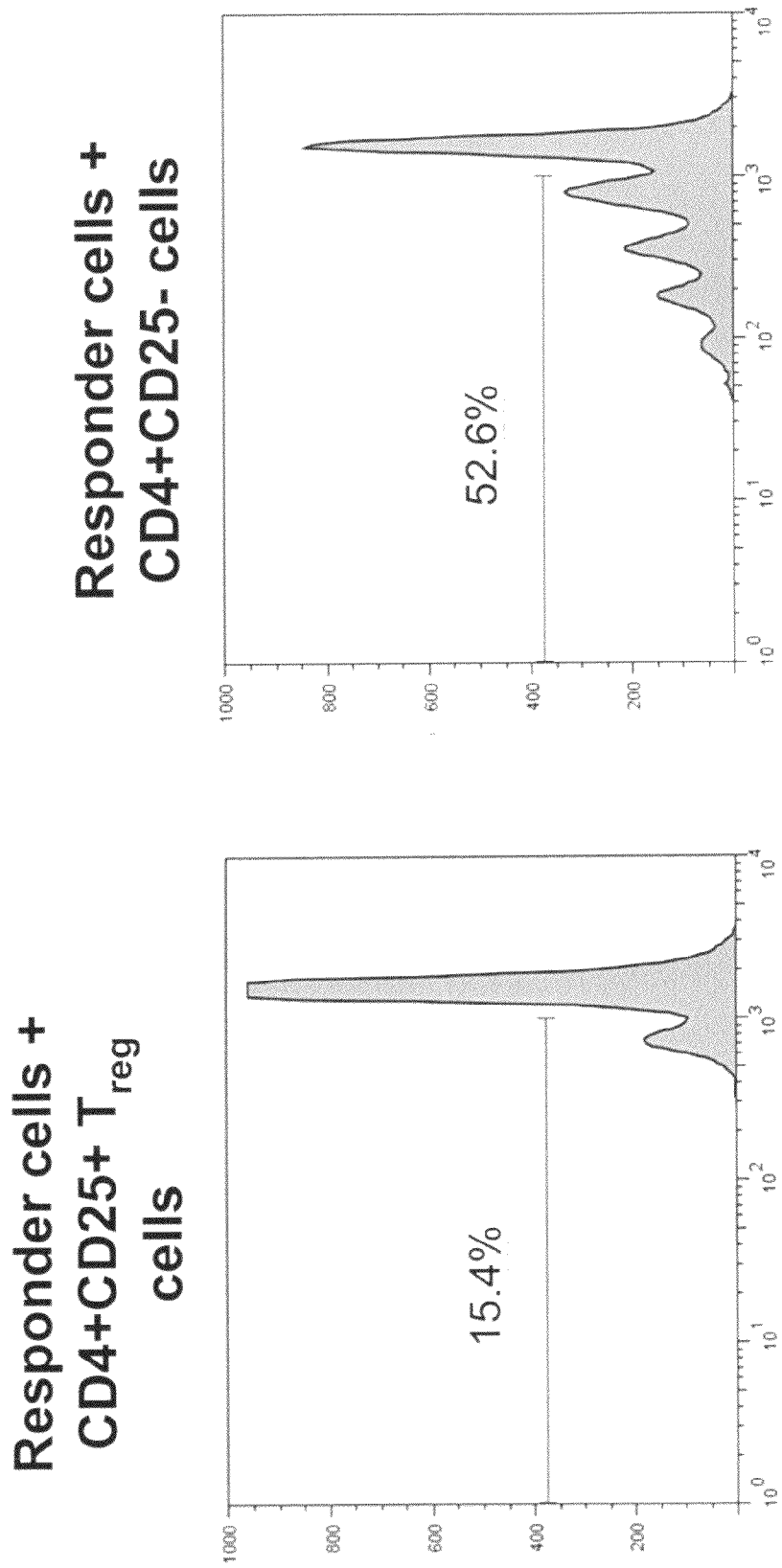
Figure 3B:
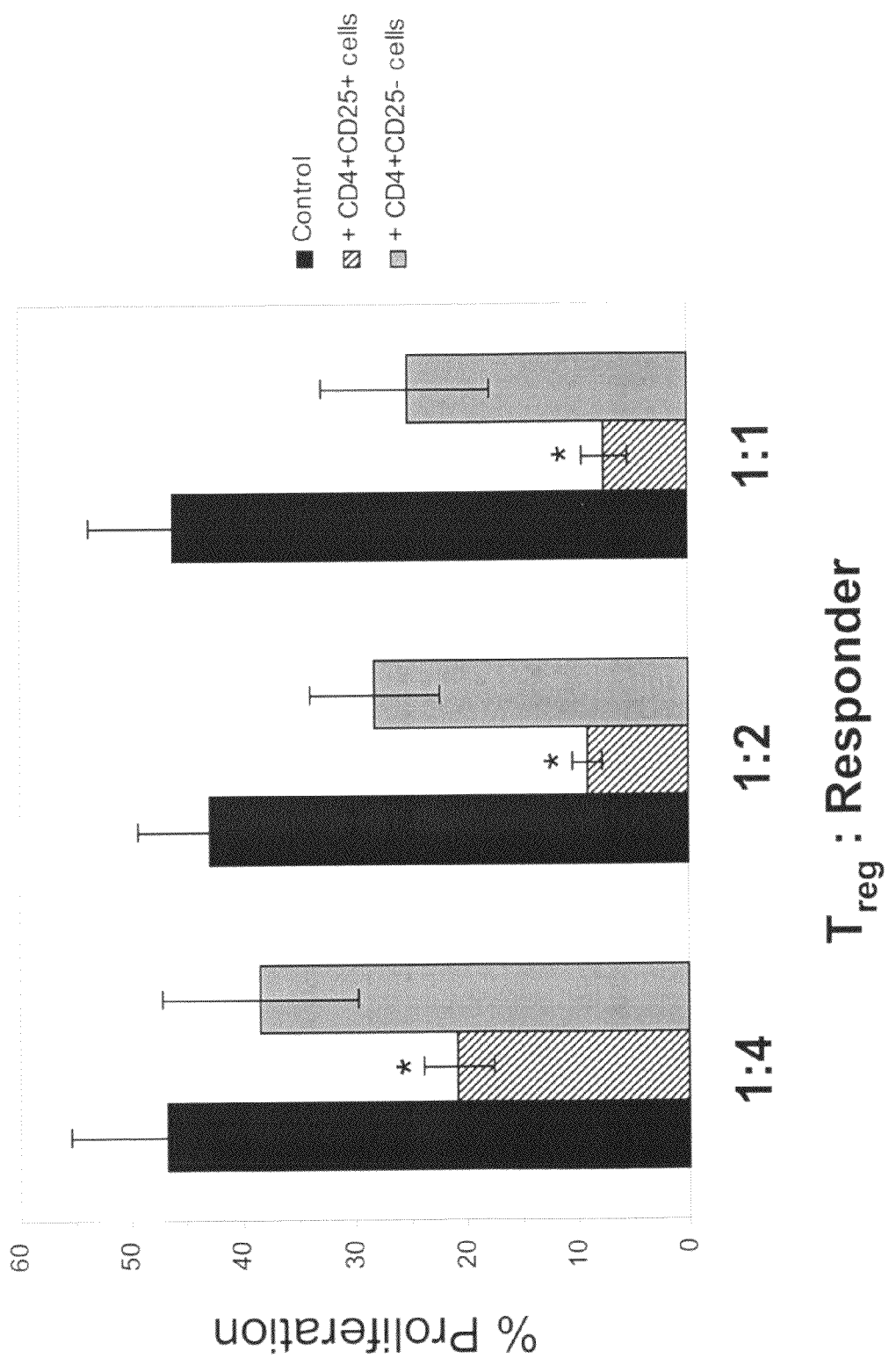
In FIG. 3(B), the proliferation data from all three regulatory T cell: responder ratios are presented for regulatory T cells ($CD4^+CD25^+$) as well as the two controls (control T cells and $CD4^+CD25^-$ cells). The data are shown as the mean % proliferation of responder cells from three separate experiments. Asterisks indicate statistically significant differences between control T cell samples and samples with added $CD25^+$ cells (normalized to samples containing CFSE-labeled responder cells only, one-tailed t-Test, $p<0.05$).
Figure 4:
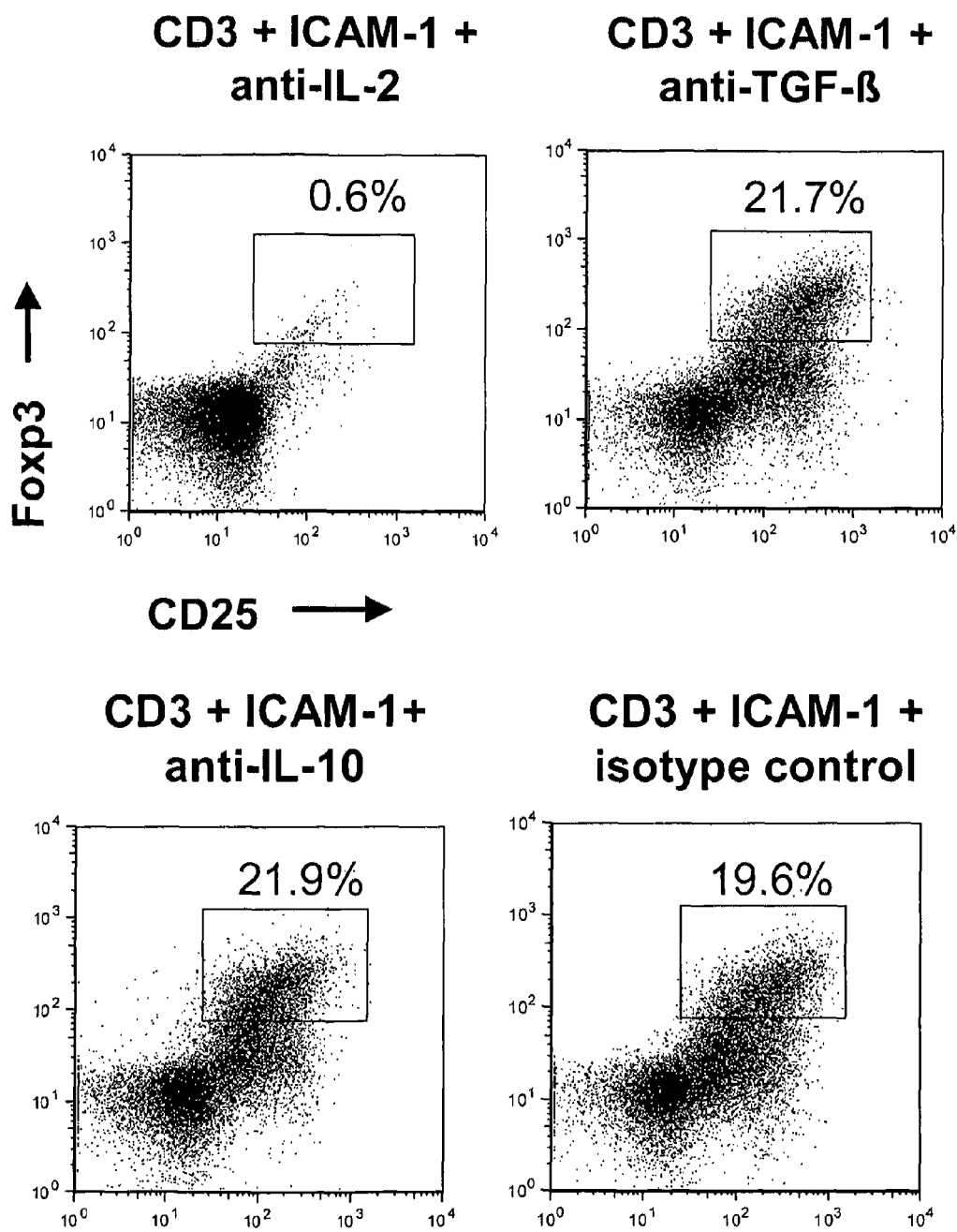
FIG. 4 shows differentiation of naïve $CD4^+$ T cells to regulatory T cells is dependent upon secreted IL-2, but not IL-10 or TGF-β. Blocking anti-IL-2, anti-IL-10, anti-TGF-β, or isotype control antibodies were added to CD3 plus ICAM-1 stimulated cultures at Day 0 and Day 5 of stimulation at 20 µg/mL. Representative of four experiments.

When the $CD4^+CD25^+$ cells that had differentiated in ICAM-1-co-stimulated cultures were added to the responder cells, responder cell proliferation was greatly diminished. FIG. 3(A) shows a suppression assay performed at a regulatory T cell: Responder cell ratio of 1:4. In this experiment, only 15.4% of the responder cells divided when $CD4^+CD25^+$ regulatory T cells were added to the culture and only one round of cell division occurred. In contrast, when responder cells only were measured or when control T cells or $CD4^+CD25^-$ cells were added to the culture, over 50% of the responder cells divided and multiple rounds of cell division were observed. The $CD4^+CD25^+$ regulatory T cells inhibited responder cell proliferation at each regulatory T cell to Responder ratio, and a dose-dependent effect was observed (FIG. 3(B)). The $CD4^+CD25^-$ cells also inhibited responder cell proliferation in some experiments. However, this inhibition was much weaker than inhibition by the $CD4^+CD25^+$ regulatory T cells and could possibly be due to contamination of $CD4^+CD25^-$ cells in the $CD4^+$ $CD25^-$ population (purity of the $CD4^+CD25^-$ population was greater than 90%, data not shown) or to the presence of $CD25^-$ cells with suppressive capabilities.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

From the foregoing, it will be seen that this invention is one well adapted to attain all ends and objectives herein above set forth, together with the other advantages which are obvious and which are inherent to the invention. Since many possible embodiments may be made of the invention without departing from the scope thereof, it is to be understood that all matters herein set forth or shown in the accompanying figures are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A method for generating a purified regulatory T cell composition having a $CD4^+CD25^+Foxp3^+$ phenotype from naive T cells having $CD4^+CD45RA^+RO^-$ $CD11a^{lo}CD27^+$ phenotype comprising:
   providing a naive T cell composition of the $CD4^+CD45RA^+RO^-CD11a^{lo}CD27^+$ phenotype;
   stimulating a T cell receptor on said naive T cells; and
   stimulating ICAM-1 on said naive T cells using anti-CD54 antibodies;
   wherein said stimulating is performed ex-vivo and causes said naive T cells to differentiate into a first composition containing regulatory T cells;
   and
   substantially separating said regulatory T cells from said first composition to form a purified regulatory T cell composition.

2. The method of claim 1 wherein said T cell receptor is stimulated using an anti-CD3 antibody.

3. The method of claim 1 wherein said T cell receptor is stimulated using an antigen-specific activator.

4. The method of claim 1 wherein said ICAM-1 is stimulated using an immobilized anti-CD54 antibody.

5. The method of claim 1 further wherein said stimulating said T cell receptor and stimulating said ICAM-1 occurs over a period between about three days and three weeks.

6. The method of claim 1 wherein said regulatory T cells are further proliferated.

7. The method of claim 1 wherein said separating is performed using flow cytometry cell sorting or magnetic cell sorting.

8. The method of claim 1 wherein said purified composition comprises at least a 90% pure regulatory T cell composition.

9. The method of claim 1 wherein said purified composition comprises at least a 98% pure regulatory T cell composition.

10. A method for the isolation of human regulatory T cells, the method comprising:
    obtaining a cell sample comprising naïve T cells having a $CD4^+CD45RA^+RO^-$ $CD11a^{lo}CD27^+$ phenotype from a human donor,
    isolating said naive T cells from said cell sample;
    stimulating a T cell receptor on said naive T cells; and
    stimulating ICAM-1 on said naive T cells cells using anti-CD54 antibodies;
    wherein said stimulating causes said naive T cells to differentiate into a first composition containing regulatory T cells;
    and
    substantially separating said regulatory T cells from said first composition to form a purified regulatory T cell composition.

11. The method of claim 10 wherein said substantially separating step comprises contacting said cell sample with antibodies that specifically recognize CD4, CD25, and CD127; selecting for those cells that are CD4$^+$CD25$^+$CD127$^-$ to provide a purified regulatory T cell composition.

12. The method of claim 10 wherein said substantially separating step comprises removing cells expressing CD127+.

13. The method according to claim 10, wherein cell sample is a blood sample.

14. The method according to claim 10, wherein said cell sample is a lymph node sample.

15. The method according to claim 10, wherein said cell sample is a tissue sample.

16. The method according to claim 10, wherein said human donor is suffering from an aberrant immune response disorder.

17. The method according to claim 16, wherein said aberrant immune response disorder is an autoimmune disorder or allergic disorder.

18. The method according to claim 10, wherein said human donor is an organ or bone marrow transplant recipient.

* * * * *